US005337365A

United States Patent [19]

Hamabe et al.

[11] Patent Number: 5,337,365

[45] Date of Patent: Aug. 9, 1994

[54] APPARATUS FOR ACTIVELY REDUCING NOISE FOR INTERIOR OF ENCLOSED SPACE

[75] Inventors: Tsutomu Hamabe, Yokosuka; Akio Kinoshita, Fujisawa; Kazuhiro Doi, Yokohama; Kenichiro Muraoka, Yokosuka; Noriharu Sato, Katsuta, all of Japan

[73] Assignees: Nissan Motor Co., Ltd., Yokohama; Hitachi, Ltd., Tokyo, both of Japan

[21] Appl. No.: 935,100

[22] Filed: Aug. 27, 1992

[30] Foreign Application Priority Data

Aug. 30, 1991 [JP] Japan ................................ 3-220620

[51] Int. Cl.[5] ............................................ A61F 11/06

[52] U.S. Cl. ........................................ 381/71; 381/94

[58] Field of Search .................................. 381/71, 94

[56] References Cited

U.S. PATENT DOCUMENTS 4,677,676 6/1987 Ericksson ............................ 381/71
5,170,433 12/1992 Elliott et al. ......................... 381/71

FOREIGN PATENT DOCUMENTS

0361968A2 6/1989 European Pat. Off. .
3908881A1 3/1990 Fed. Rep. of Germany .
4042116A1 7/1991 Fed. Rep. of Germany .
3-203496 5/1991 Japan .................................. 381/71
3-203497 5/1991 Japan .................................. 381/71
2149614A 6/1985 United Kingdom .

OTHER PUBLICATIONS

Stephen Elliott et al., "A Multiple Error LMS Algorithm and Its Application to the Active Control of Sound and Vibration", vol. ASSP-35, No. 10, Oct. 1987, IEEE Transactions on Acoustics.

*Primary Examiner*—Curtis Kuntz
*Assistant Examiner*—Mark D. Kelly
*Attorney, Agent, or Firm*—Lowe, Price, LeBlanc & Becker

[57] ABSTRACT

An apparatus for reducing noise for an interior of enclosed space, e.g., a vehicular compartment using an FIR adaptive digital filter is disclosed in which a control circuit is provided which outputs drive signals to a plurality of loud speakers which generate control sounds to interfer with a noise sound propagated in the interior so that a performance function including terms of residual noise signals output from residual noise signal detecting microphones and drive signals to the loud speakers is minimized and contributivity of the drive signals to the performance function is changed according to an occurrence of divergence in the noise reducing apparatus.

27 Claims, 13 Drawing Sheets

$J_m = \Sigma e^2 + \beta y^2$

APPARATUS FOR ACTIVELY REDUCING NOISE FOR INTERIOR OF ENCLOSED SPACE

BACKGROUND OF THE INVENTION

1. Field of The Invention

The present invention relates generally to an apparatus for actively reducing noise for interior of enclosed space. The present invention, particularly, relates to the apparatus for actively reducing noise sound for a vehicular compartment or for a cabin of a fuselage, and so on, the noise sound being generated and propagated from a noise source, e.g., a vehicular or aircraft power source and the apparatus using an adaptive signal processing filter.

2. Description of The Background Art

A previously proposed active noise reduction apparatus is exemplified by a British Patent Application Publication No. GB 2 149 614 A published on Jun. 12, 1985.

FIG. 1 shows a circuit block diagram of the previously proposed active noise reduction apparatus described above.

In FIG. 1, an enclosed space 101 is provided with a plurality of, i.e., three loud speakers 103*a*, 103*b*, and 103*c* and a plurality of, i.e., four microphones 105*a*, 105*b*, 105*c*, and 105*d*. Each loud speaker 103*a*, 103*b*, 103*c*, and 103*d* generates a controlling sound which interferes with the noise sounds and each microphone 105*a*, 105*b*, 105*c*, and 105*d* measures a residual signal at an observing point of location of the enclosed space 101.

These loud speakers 103*a*, 103*b*, and 103*c* and microphones 105*a*, 105*b*, 105*c*, and 105*d* are connected to a signal processing unit 107. The signal processing unit 107 receives basic frequencies of the respective noise sources measured by basic frequency measuring means and input signals derived from the respective microphones 105*a*, 105*b*, 105*c*, and 105*d* and output drive signals to the loud speakers 103*a*, 103*b*, and 103*c* so that a sound pressure level in the enclosed space 101 gives a minimum value.

Although, in the enclosed space 101, three loud speakers 103*a*, 103*b*, and 103*c* and four microphones 105*a*,, 105*b*, 105*c*, and 105*d* are installed, suppose now that one loud speaker 103*a* and one microphone 105*a* are individually installed therein for easiness in explanation.

Suppose, then, that a transfer function established between the single noise source and the single microphone 105*a* is denoted by H, a transfer function established between the loud speaker 103*a* and microphone 105*a* is denoted by C, and a sound source information generated by the single noise source is denoted by $X_p$.

At this time, a noise signal E as the residual noise sound observed by the microphone 105*a* is expressed below:

$$E = X_p \cdot H + X_p \cdot G \cdot C$$

In the above equation, G denotes a transfer function required to extinguish or cancel the noise sound. Theoretically, at a sound extinguishing (canceling) point (at a position at which the microphone is disposed), when the noise is completely canceled, E=0. At this time, G is derived from the above-equation.

$$G = -H/C$$

Filter coefficients in the signal processing unit 107 are adaptively updated on the basis of G derived so that the power of microphone detection signal becomes minimum. A technique of deriving the filter coefficients so that the power of microphone detection signal E becomes minimum includes an LMS (Least Mean Square) algorithm which is a kind of a steepest descent method.

As shown in FIG. 1, in a case where the plurality of microphones are disposed, the control for the output signals for the loud speakers is such that a total sum of the powers of signals detected by, e.g., respective microphones 105*a* , 105*b*, 105*c*, and 105*d* becomes the minimum.

A Multiple Error Filtered-X LMS algorithm (hereinafter, LMS is referred to as Multiple Error Filtered-X LMS algorithm) will specifically be explained below.

That is to say, suppose now that a noise signal is denoted by $e_l(n)$ detected by an l number microphone 105*a* (105*b*, 105*c*, . . . ), a noise signal is denoted by $e_{pl}(n)$ detected by the l number microphone 105*a* (105*b*, 105*c*, . . . ) when no control sound is present from any one of the loud speakers 103*a*, 103*b*, and 103*c*, a filter coefficient is denoted by $C_{lmj}$ when a j number term of $j=0, 1, 2, \ldots, J_c-1$) a transfer function (a finite form of an impulse response function) established between an m number loud speaker 103*a* (103*b*, . . . ) and an l number microphone (evaluating point), i.e., working position is represented by a digital filter, a reference signal, i.e., sound source information signal $x_p(n)$, and a coefficient of the i number ($i=0, 1, 2, 3, \ldots, I_k-1$) of an adaptive processing filter which drives the m number of loud speaker 103*a* (103*b*, 103*c*, . . . ), inputting the reference signal $x_p(n)$ is denoted by $W_{mi}$.

At this time, the equation (1) of attached Table 1 of mathematical equations is established.

Next, suppose furthermore that a performance function (a variable to make the noise signal $e_l(n)$ minimum) Je is expressed as in the equation (2) of attached Table 1 of the mathematical equations, the performance function being based on the equation of (1).

In order to derive the filter coefficients $W_{mi}$ which makes the performance function Je minimum, the LMS algorithm is adapted. That is to say, the filter coefficient $W_{mi}$ is updated with a value of a partial differential of Je with respect to each filter coefficient $W_{mi}$.

Then, from the equation (2), the partial differential is calculated as in the equation (3) of attached Table 1 of the mathematical equations.

On the basis of the equation (1), the equation (4) of Table 1 of the mathematical equations is established.

If a right side of the equation (4) is substituted by $r_{lm}(n-i)$, an updating equation of the filter coefficients can be derived according to the equation (5) of attached table 1 of the mathematical equations including a weight coefficient of $\gamma_l$.

As appreciated from the equation of (5), a stability and divergence of the LMS algorithm are predominated in an equation (6) of attached Table 1 of the mathematical equations, a convergence coefficient $\alpha$, and the weight coefficient $\gamma_l$.

Although the above-equation (6) is dependent on a system characteristic to be controlled and a setting method of the microphones in the system, such a transfer function (finite impulse response) $C_{lm}$ as established from one of the loud speakers to one of the microphones is treated as constant.

However, aging effects of each microphone 103*a*, 103*b*, - - - and each loud speaker 105*a*, 105*b*, - - -cause phase characteristics of the respective speakers and loud speakers to be varied so that the transfer function $C_{lm}$ is accordingly varied. Consequently, a convergence characteristic of the updating equation of (5) becomes extremely unstable. If surrounding conditions of the equation (5) becomes worsened, a rise in a sound pressure level at the evaluating point may occur and, so called, a divergence phenomenon may occur at the evaluating point.

In this case, it may be possible for the convergence coefficient $\alpha$ to become smaller so as to suppress the divergence. As the convergence coefficient $\alpha$ becomes significantly smaller, the number of times that calculations of the equation (5) is carried out until reaching the convergence becomes larger. Consequently, the convergence characteristic may become moderate or dull.

Therefore, an algorithm in which an alternative performance function Jm is used has been proposed in an English paper of IEEE TRANSACTIONS 0N ACOUSTICS SPEECH AND SIGNAL PROCESSING, VOL. ASSP-35, No. 10, October 1987.

That is to say, drive signals for the speakers are added to the old minimizing performance function and $\beta$ is multiplied by the speaker drive signals to establish the alternative performance function as in the equation (7) of attached Table 1 of the mathematical equations.

It is noted in all equations from (1) to (7 ) that x(n) denotes the reference signal at a sampling time of n, $e_{pl}$ (n) denotes a residual noise detection signal (primary sound) detected by the l number microphone when no control sound (secondary sound) is received from any one of the loud speakers, $C_{lmj}$ denotes a filter coefficient when a j number term of the transfer function between the l number microphone and m number loud speaker is represented by a digital filter, $y_m(n)$ denotes the output of the m number loud speaker, $e_l$ (n) denotes an error signal detected by the l number microphone, $W_{mi}$ denotes the i number adaptive filter coefficient for the m number loud speaker, L denotes a number of microphones, M denotes a number of speakers, $\alpha$ denotes a convergence factor (coefficient), and $\beta$ denotes an effort coefficient.

In the way described above, when the term of the speaker driver signal is added into the performance function Jm , the coefficient (effort coefficient $\beta$) to determine a length of a vector which serves to try to keep the adaptive filter coefficient not go far away from an origin 0 can be given since the performance function makes the speaker drive signal smaller.

That is to say, as shown in FIGS. 2 and 3, a point determined by the adaptive filter coefficients $W_{mi}$ tries to return to the origin, with the vector which tries to return to the origin given to the vector based on the convergence coefficient $\alpha$. Hence, when the divergence phenomenon occurs, the performance function can be approached to a minimum.

FIG. 3 shows a control algorithm in a case where the adaptive filter has two variable filter coefficients $W_0$, $W_1$.

In FIG. 3, $J_1$ denotes a first term of $\Sigma e^2$ in the performance function of $J_m$, $J_2$ denotes a second term of $\beta y^2$, $W_{opt}$ denotes optimum filter coefficients of $W_0$ and $W_1$ according to the performance function J, $\Delta W_y$ denotes a resultant vector of $\beta y^2$ and $\Delta W_e$ denotes a resultant vector of $\beta y^2$.

However, even in the case where, as described above, the noises are controlled by means of the algorithm having the term multiplied by the effort coefficient $\beta$ when the transfer function $C_{lm}$ is varied, the performance function cannot always be returned to the minimum position since the effort coefficient $\beta$ is fixed, as shown in FIGS. 2 and 3, and a slight deviation may occur. Thus, the insufficient noise control may result.

SUMMARY OF THE INVENTION:

It is, therefore, a principal object of the present invention to provide an improved apparatus for actively reducing noise in an interior of enclosed space which can suppress divergence of control sound by the apparatus itself and can provide a more appropriate control of reducing the noise.

The above-described object can be achieved by providing an apparatus for actively reducing noise for an interior of enclosed space, comprising: a) control sound source means for generating a control sound to be interfered with the noise according to a drive signal input thereto so as to reduce the noise propagated into the interior of enclosed space at an evaluating area in the interior of enclosed space at which a degree of a residual noise sound is evaluated; b) residual noise detecting means for detecting the residual noise sound at a predetermined area of the interior of the enclosed space after the noise interference is carried out by the control sound source means and outputting the detected residual noise sound as a residual noise signal; c) reference signal detecting means for detecting a signal related to a noise source and processing the detected signal as a reference signal; d) controlling means for outputting the drive signal to said control sound source means on the basis of the output residual noise signal of said residual noise detecting means, the reference signal of said reference signal detecting means, and the drive signal output from the controlling means itself to the control sound source so that a performance function is minimized, said performance function being established thereby on the basis of the output residual noise signal of said residual noise detecting means and the drive signal output to said control sound source means; and e) changing means for changing a contributivity of the drive signal output to said control sound source means to the performance function.

The above-described object can also be achieved by providing an apparatus for actively reducing noise for an interior of enclosed space, comprising: a) control sound source means for generating a control sound to be interfered with the noise according to a drive signal input thereto so as to reduce the noise propagated into the interior of enclosed space at an evaluating area in the interior of enclosed space at which a degree of a residual noise sound is evaluated; b) residual noise detecting means for detecting the residual noise sound at a predetermined area of the interior of the enclosed space after the noise interference is carried out by the control sound source means and outputting the detected residual noise sound as a residual noise signal; c) reference signal detecting means for detecting a signal related to a noise source and processing the detected signal as a reference signal; d) controlling means for outputting the drive signal to said control sound source means on the basis of the output residual noise signal of said residual noise detecting means and the reference signal of said reference signal detecting means so that an performance function is minimized, said performance function being established thereby on the basis of the output residual noise signal of said residual noise detecting means and the drive signal output to said control sound source means and including a term of the drive signal output to said control sound source means multiplied by an effort coefficient; and e) changing means for changing the effort coefficient so that a contributivity of the drive signal output to said control sound source means to the performance function is varied The above-described object can also be achieved by providing an apparatus for actively reducing noise sound for a vehicular compartment, comprising: a) an electrical-acoustic transducer which generates a control sound to be interfered with the noise sound in response to a drive signal so as to reduce the noise sound at respective evaluating points of location in the vehicular compartment; b) an acoustic-electrical transducer which detects a residual noise at predetermined positions of the vehicular compartment after the interference of the control sound with the noise sound by said electrical-acoustic transducer and output a residual noise signal indicating the detected residual noise; c) detecting means for detecting a signal related to a noise generating state from a vehicular noise source and outputting a discrete reference signal indicating the signal related to the noise generating state; d) controlling means for establishing an performance function on the basis of the residual noise signal and transducer drive signal and for outputting the drive signal to said electrical-acoustic transducer so that the performance function is minimized on the basis of the residual noise signal of said acoustic-electrical transducer, the reference signal of said detecting means, and, furthermore, the electrical-acoustic transducer drive signal; e) divergence detecting means for detecting an occurrence of divergence of the control sounds at evaluating points of location and outputting a divergence indicative signal whenever the divergence occurs; and f) contributivity changing means for changing a contributivity of the electrical-acoustic transducer drive signal to the performance function in response to the divergence indicative signal derived from said divergence detecting means.

DESCRIPTION OF THE PREFERRED EMBODIMENT:

Reference will hereinafter be made to the drawings in order to facilitate a better understanding of the present invention.

Figure 1:
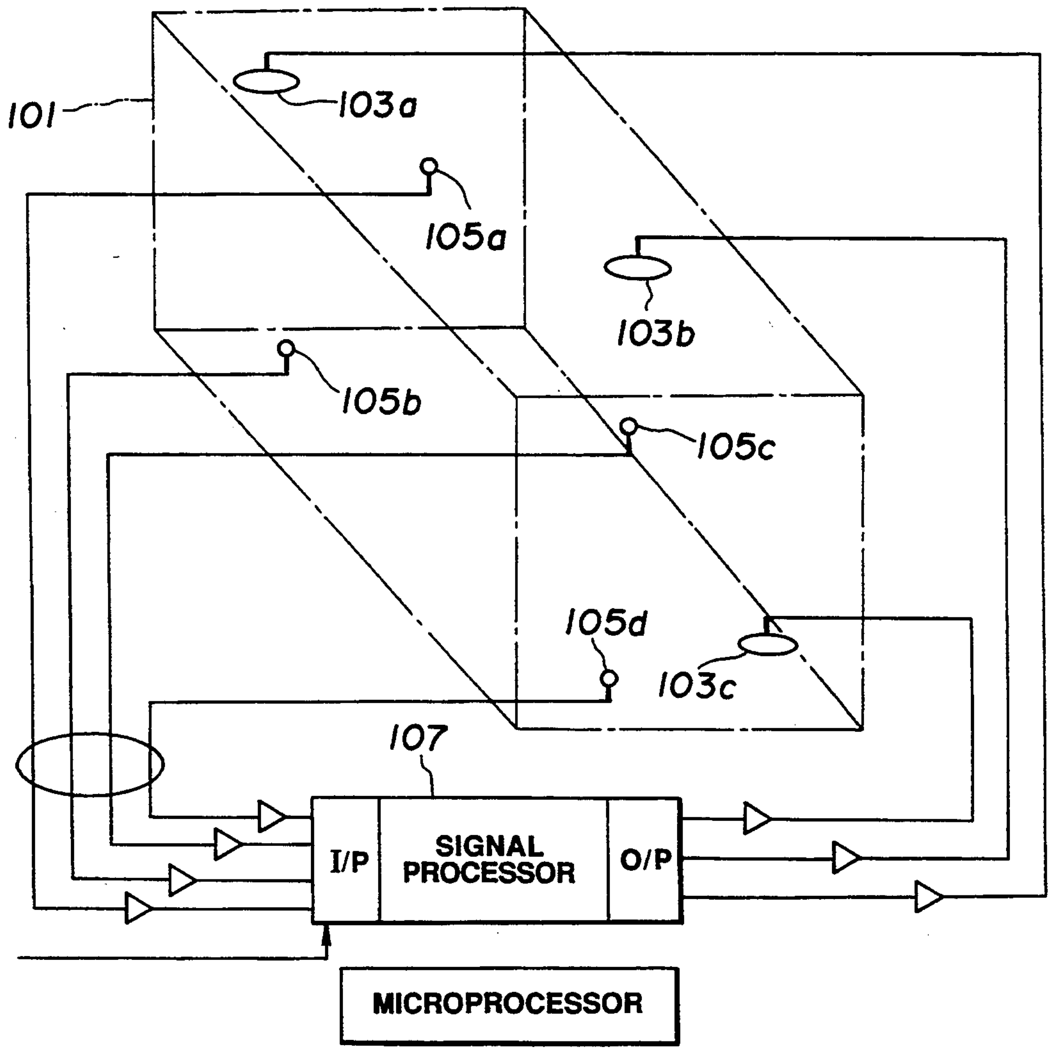
FIG.1 (PRIOR ART)
FIG. 1 is a circuit block diagram of a previously proposed noise reduction apparatus for an interior of enclosed space described in British Patent Application Publication No. GB 2 149 614 A.
Figure 2:
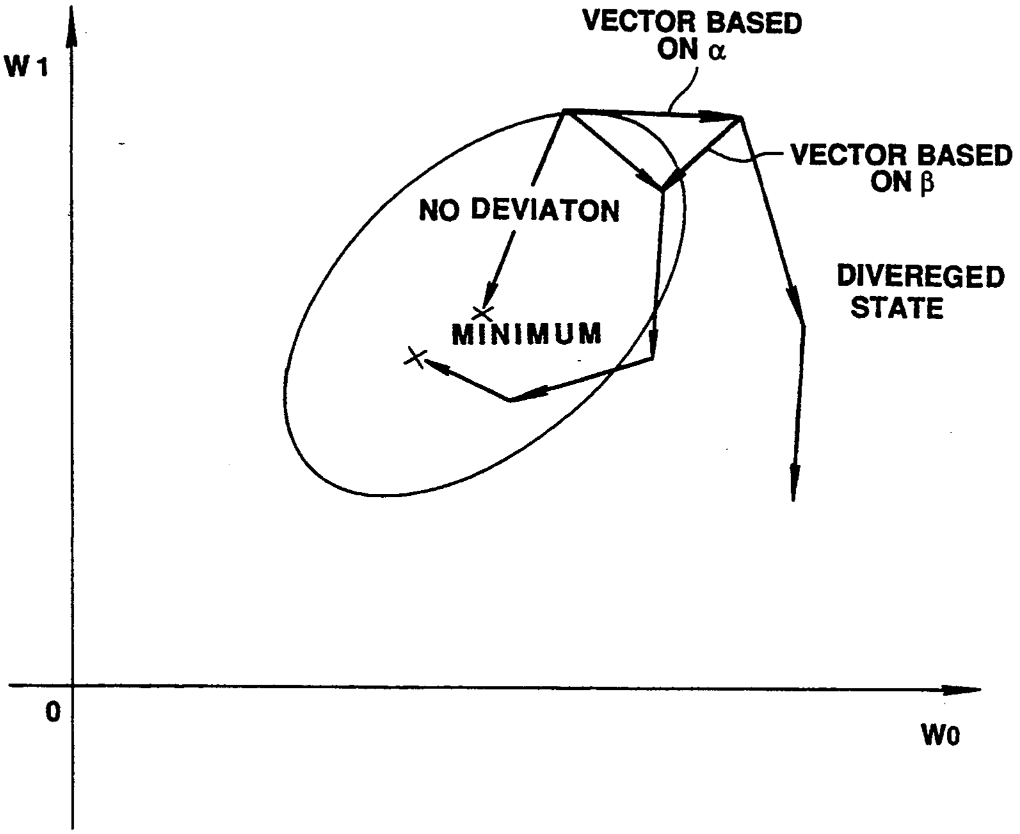
FIG.2 (PRIOR ART)
FIGS. 2 and 3 are explanatory views of a performance function and steepest descent method of LMS algorithm in the previously proposed actively noise reducing apparatus shown in FIG. 1.
Figure 3:
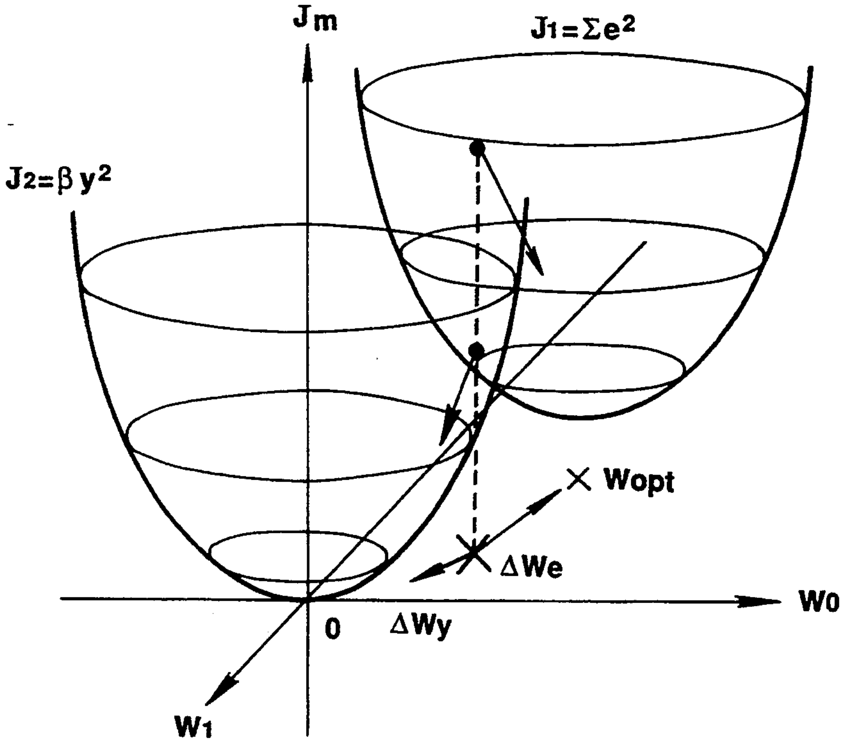
FIG.3 (PRIOR ART)

FIGS. 1 through 3 have already been explained in the Description of the Background Art.

Figure 4:
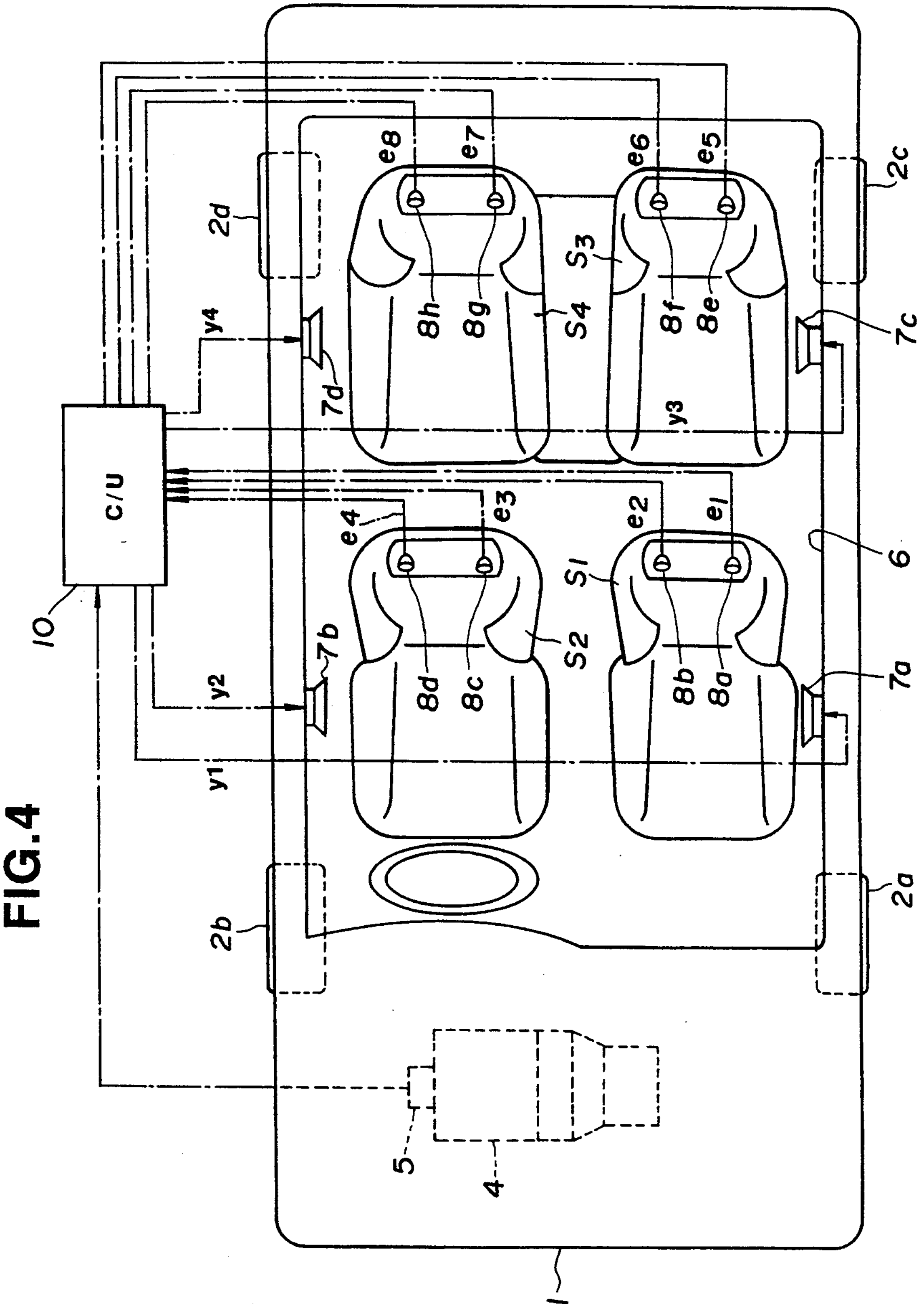
FIG. 4 is a schematic wiring diagram of a noise actively reducing apparatus in a preferred embodiment according to the present invention applicable to a vehicular compartment.

FIG. 4 shows a whole circuit arrangement of a noise actively reducing apparatus in a preferred embodiment according to the present invention applicable to a vehicular compartment.

The vehicular compartment is defined as an interior of an enclosed space.

As shown in FIG. 4, a vehicle body 1 is supported by means of front tire wheels 2a, 2b, and rear tire wheels 2c, 2d, the front tire wheels 2a, 2b being driven according to a power of an engine 4 mounted at a front part of the vehicle body 1. Thus, the vehicle is a front engine front drive type (FF) automotive vehicle.

Noises appearing in the vehicular compartment 6 are propagated from , e.g., a noise source of the engine 4. Noise generating state detecting means is constituted by, e.g., a crank angle sensor 5.

A pulse formed detection signal x corresponding to an engine crankshaft rotation angle correlated to the engine noise is output from the crank angle sensor 5. In the case of a four-stroke and four-cylinder engine which provides the noise source, the pulse formed detection signal is output whenever the crankshaft has rotated through 180.

It is noted that since the noise generating state detecting means can detect only a signal related to the noise generating state of the noise source, an output signal of a engine vibration responsive sensor installed on, e.g., an exterior of the engine, an ignition pulse signal for the engine cylinders, a rotation speed of the crankshaft, or alternatively engine revolution speed signal detected by engine revolution speed sensor may be used.

On the other hand, four loud speakers 7a, 7b, 7c, and 7d are disposed on door portions (predetermined positions or area) of the vehicle body 1 opposing front occupant seats S1, S2, S3, and S4, the loud speakers being control sound sources in the vehicle compartment 6 which serves as an acoustic enclosed space of the vehicle body 1.

A plurality (eight) of microphones 8a through 8h are disposed on head rest positions (defined as evaluating area or evaluating points) of respective occupant seats S1 through S4 as residual noise detecting means.

The residual noise in the vehicle compartment 6 input to these microphones 8a through 8h is transmitted to a control unit 10 in the form of electrical noise signals $e_1$ through $e_8$ according to its sound pressure level.

The output signals of the crank angle sensor 5 and microphones 8a through 8h are individually transmitted to the control unit 10 as controlling means.

Drive signals $y_1$ through $y_4$ output from the control unit 10 are individually transmitted to the loud speakers *7a* through *7d*. Thus, the speakers *7a* through *7d* output acoustic signals (control sounds) toward the vehicular compartment 6.

Figure 5:
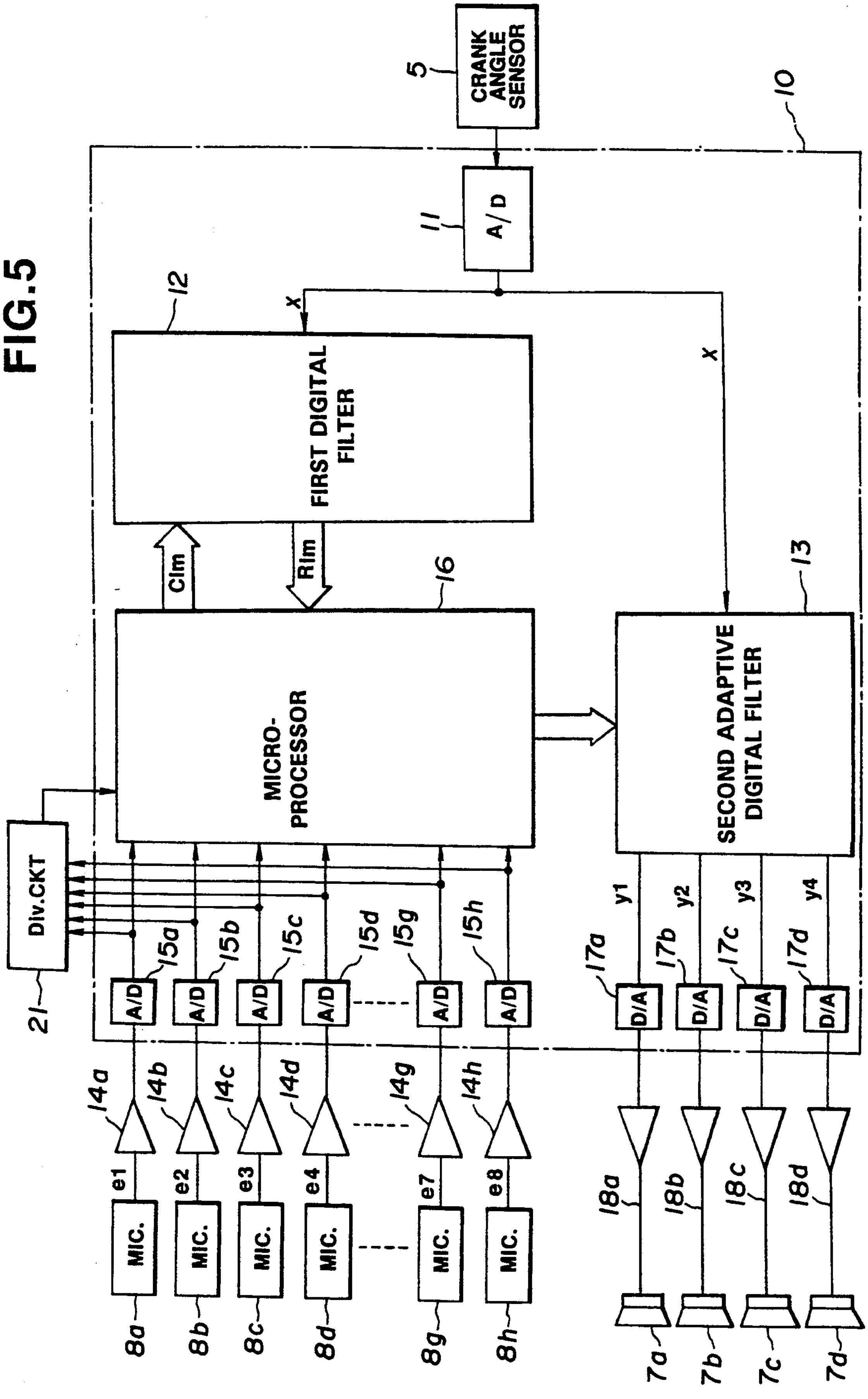
FIG. 5 is a circuit block diagram of the actively noise reducing apparatus in the preferred embodiment shown in FIG. 4.

FIG. 5 is a circuit block diagram of the control unit and peripheral sensors and transducing means in the noise actively reducing apparatus in the preferred embodiment shown In FIG. 4.

The control unit 10, as shown in FIG. 5, includes: a first digital filter 12; a second digital filter (adaptive digital filter) 13; a microprocessor 16; and a divergence detection (or detecting) circuit 21 as divergence detecting means.

The pulse formed detection signal x input from the crank angle sensor 5 is converted into a digital signal by means of an analog-to-digital (A/D) converter 11 so that the digital signal as a discrete reference signal x is input to the first digital filter 12 and the second digital filter 13.

Referring to FIG. 5, the noise signals $e_1$–$e_8$ of the output signals of the microphones 8a through 8h are amplified by means of amplifiers 14a through 14h and A/D converted by means of A/D converters 15a through 15h (A/D means analog-to-digital). The A/D converted signals by means of the analog-to-digital converters 15a through 15h are input to a microprocessor 16 together with the output signal of the first digital filter 12. The drive signals $Y_1$ through $y_4$ input from the second digital filter 13 are D/A converted by means of the D/A converters 17a through 17d and transmitted to the respective loud speakers *7a* through *7d* via amplifiers 18a through 18d.

The first digital filter 12 receives the reference signal x and generates a filtered reference signal $r_{lm}$ (refer to equations (18) and (19) to be described later), the filtered reference signal being filter processed according to a number of combinations of transfer functions between the microphones 8a through 8d and speakers *7a* through *7d*.

The second digital filter 13 is functionally provided with a plurality of individual filters according to the number of output channels to the speakers *7a* through *7d*. The second digital filter 13 receives the reference signal x, carries out an adaptive signal processing on the basis of filter coefficients (refer to equation (19) as will be described later) set at the present time, and outputs the speaker drive signals $y_1$ through $y_4$.

The microprocessor 16 receives the noise signals $e_1$ through $e_8$ and filter processed reference signal $r_{lm}$ and updates the filter coefficients in the second digital filter 13 using the LMS algorithm which is a kind of a steepest descent method.

The above-described filtered reference signal of $r_{lm}$ includes $C_{lm}$ representing the transfer functions between the loud speakers *7a* through *7d* and microphones 8a through 8h as a filter coefficient of the digital filter. The microprocessor 16 outputs the signal used to drive the control sound source.

A theory of operation of noise reduction by means of the control unit 10 will be described below using general formulae.

Now suppose that $e_l$ (n) denotes one noise signal detected by means of an l number microphone, d(n) denotes a residual noise detection signal detected by the l number microphone when no control sound (secondary sound) from any one of the loud speakers *7a* through *7d* is present, $C_{lmj}$ denotes a filter coefficient corresponding to the j number term of the transfer function $H_{lm}$ as the finite form of impulse response form (i=0, 1, 2, . . . , J −1), and $W_{mi}$ denotes the i number coefficient (i=0, 1, . . ., I−1) of the adaptive signal processing filter 18 receiving the reference signal x and driving the m number loud speaker.

The equation (8) of attached Table 2 of the mathematical equations is, then, established.

In the equation (8), any term to which (n) is attached denotes a sampled value at a sampling time of n and M denotes the number of loud speakers (in the preferred embodiment, four), J denotes the number of taps of the filter coefficients $C_{lm}$ in the first digital filter 12, and I denotes the number of the taps of the filter coefficient $W_{mi}$ of the adaptive processing filter 13.

In the equation (8), the term at the right side thereof $[\Sigma W_{mi} \cdot x(n-J-i)]$ $(=y_m)$ represents the output of the second digital filter 13 when the reference signal x is received, then, the term of $[\Sigma C_{lmj}\{\Sigma W_{mi} \cdot x(n-j-i)\}]$ represents a signal when a signal energy input to the m number speaker is output from the speaker as an acoustic energy and is reached to the l number microphone via the transfer function of $c_{lm}$ in the vehicle compartment 6, and the whole right side thereof represents a total sum of the control sounds arriving at the l number microphone since the arrival signal at the l number microphone is added to all speakers.

Next, a performance function Jm (variable to minimize the error signal) can be expressed as in the equation (9) of attached Table 2 of the mathematical equations.

In the equation (9), $y_m(n)$ denotes the speaker drive signal and is expressed as in the equation (10) of attached Table 2 of the mathematical equations.

In the preferred embodiment, the performance function Jm includes the term of $y_m$ (n) which indicates the m number speaker drive signal. An effort coefficient $\beta^m$ is used to multiply the term of the speaker drive signal $y_m(n)$. It is noted that L denotes the number of microphones (in the preferred embodiment, eight).

In order to derive the filter coefficient $W_{mi}$ which minimizes the performance function Jm, the LMS algorithm is adopted, in the preferred embodiment.

In other words, each present filter coefficient $W_{mi}$ is updated with a value of the partial differential for the performance function Jm with respect to each filter coefficient $W_{mi}$.

Substituting the equations (8) and (9) into the equation (10), the equation (11) of attached Table 2 of the mathematical equations is established.

The adaptation algorithm, then, repeatedly carries out the updating operation on the basis of the equation (12) of attached Table 2 of the mathematical equations.

In the equation of (12), according to the Multiple Error Filtered-X LMS algorithm the equation (13) of attached Table 2 of the mathematical equations is already established.

In the equation (13), the equation (14) of attached Table 3 of the mathematical equations is established.

In the equation of (14), the equation (15) of attached Table 3 of the mathematical equations is established.

It is noted that, in the equation (14), the equation (16) of attached Table 3 of the mathematical equations is established.

Then, the equation (14) can also be expressed as in the equation (17) of attached Table 3 of the mathematical equations.

The equation (13) can also be expressed as in the equation (18) of attached Table 3 of the mathematical equations according to the equations (14), (15), and (16).

Then, the equation (12) can be substituted as in the equation (19) of attached Table 3 of the mathematical equations.

It is noted that $\alpha$ denotes the convergence coefficient, relates to a speed at which the filter can optimally be converged, and relates to a stability of control at the filter convergence speed. Although the convergence coefficient $\alpha$ is handled as a mere constant, a different coefficient for each different filter coefficient $\alpha_{mi}$ can be set or alternatively the convergence coefficient $\alpha_l$ including the weight coefficient $r_l$ may be used.

In the way described above, the speaker drive signals $y_1(n)$–$y_4(n)$ are formed so as to always minimize a sum of a square sum of the input noise signals $e_1(n)$ through $e_8(n)$ and a square sum of the drive signals $y_m(n)$ by sequentially updating the filter coefficients $W_{mi}(n+1)$ of the second digital filter 13 in accordance with the LMS adaptive algorithm on the basis of the outputs of the noise signals $e_1(n)$ through $e_8(n)$ output from the microphones 8a through 8h and reference signal x(n) based on the output of the crank angle sensor 5. This drive signals $y_1(n)$ through $y_4(n)$ are supplied to the respective loud speakers 7a through 7h. The output control sounds through the speakers cause the noises propagated into the vehicle compartment 6 to be canceled.

On the other hand, in the preferred embodiment, since the term of the speaker drive signals of $y_m(n)$ is added in the performance function Jm, as shown in FIG. 2 and FIG. 3, and the speaker drive signals are decreased when the control state enters the divergence state, the vector which corresponds to the effort coefficient $\beta$ and which directs toward the origin 0 is given to the adaptive filter coefficient which tends to become far away from the origin 0.

When, therefore, the divergence phenomenon occurs, a magnitude of the vector which corresponds to the effort coefficient $\beta$ and directs toward the origin 0 is increased and the level of the speaker drive signals is decreased so as to suppress the divergence occurrence.

It is time for the magnitude of effort coefficient $\beta$ to be varied when the divergence detecting circuit 21 detects or predicts the occurrence of divergence or tendency or possibility of occurrence of divergence.

A divergence detecting circuit 21 is an example of the divergence detecting means.

It is noted that the divergence detecting circuit 21 may be constituted by a manually operable switch which is turned on to produce a divergence supression command signal by an occupant of the vehicle compartment 6 when the occupant placed at the evaluating area perceives the occurrence of divergence so that a contributivity of the speaker drive signal to the performance function is manually or spontaneously (automatically) changed or varied.

Figure 6:
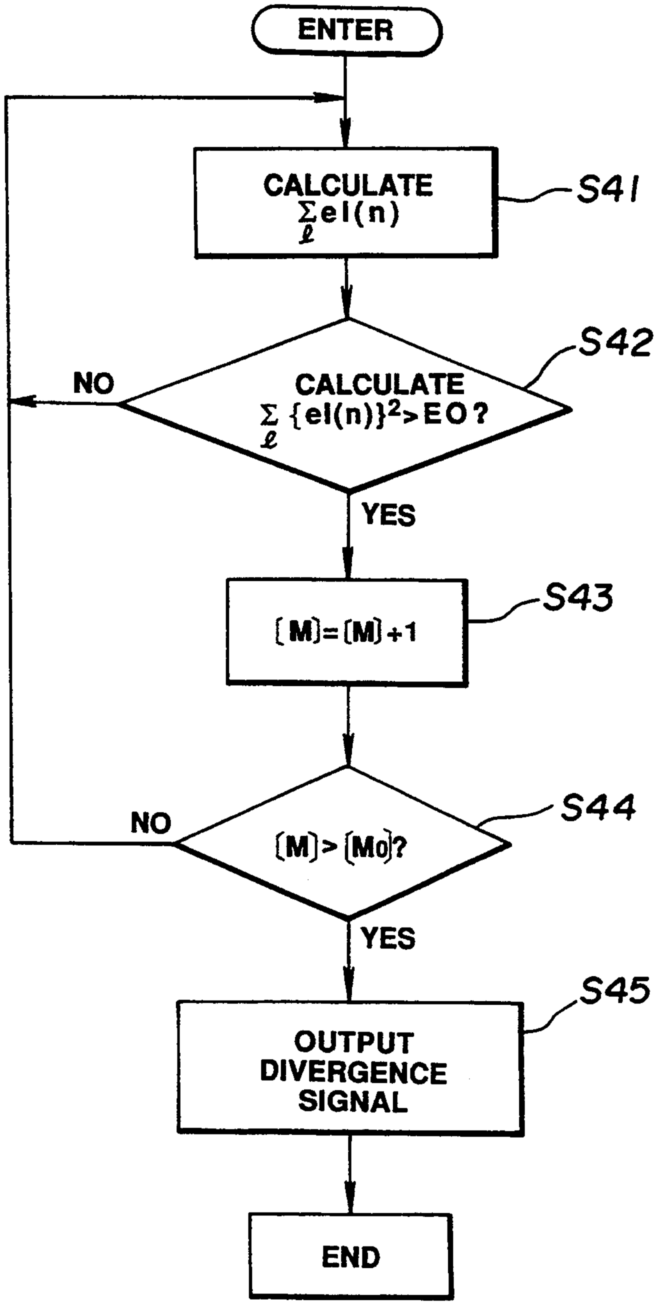
FIG. 6 is a flowchart of detecting a divergence phenomenon executed by a divergence detecting circuit shown in FIG. 5.

FIG. 6 shows a flowchart of detecting the occurrence of divergence by the divergence detecting circuit 21 according to the residual noises perceived by the microphones 8a through 8h.

The detecting circuit 21 determines the occurrence of divergence when the number of times the square sum of the outputs of the noise signals $e_1(n)$ through $e_8(n)$ output from the microphones 8a through 8h exceeds a predetermined value and outputs a divergence perception signal to the microprocessor 16.

That is to say, if the system is activated, in a step S41, the circuit 21 calculates the square sum $\Sigma\{e_l(n)\}^2$ of the noise signals $e_1(n)$ through $e_8(n)$.

Next, in a step S42, the circuit 21 determines whether the square sum $\Sigma\{e_l(n)\}^2$ of the noise signals $e_1(n)$ through $e_8(n)$ exceeds a predetermined value E0. If not exceed, the routine returns to the step S41. If exceed (YES) in the step S42, the routine goes to a step S43. In the step S43, the circuit 21 increments the number of times [M] by one, the number of times [M] being that the square sum of $\Sigma\{e_l(n)\}^2$ of the noise signals $e_1(n)$ through $e_8(n)$ exceeds a predetermined value [$M_0$]. If not exceed (NO) in the step S44, the routine returns to the step S41. If exceed (YES), the routine goes to a step S45 in which the divergence detection (indicative) signal is transmitted to the microprocessor 16.

The effort coefficient $\beta$ is varied according to the number of times the divergence has been detected.

Next, a procedure of varying the effort coefficient $\beta$ according to the occurrence of divergence will be described below.

Figure 7:
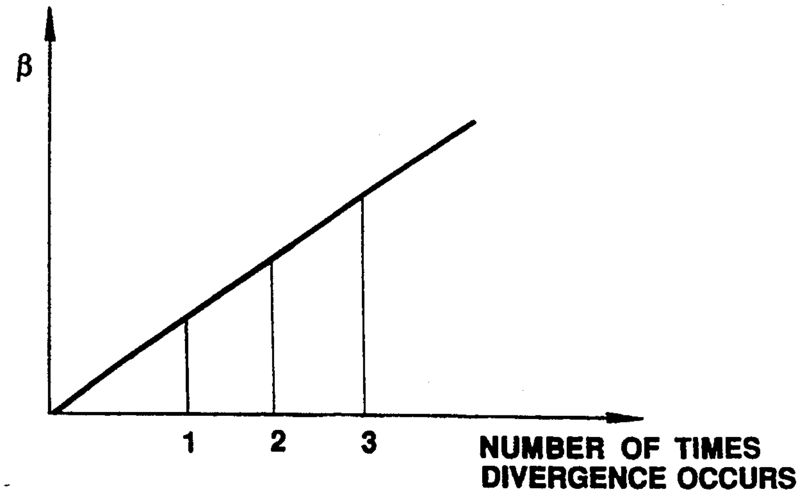
FIG. 7 is a characteristic graph of an effort coefficient varying with respect to a linear number of occurrences of divergences.
Figure 9:
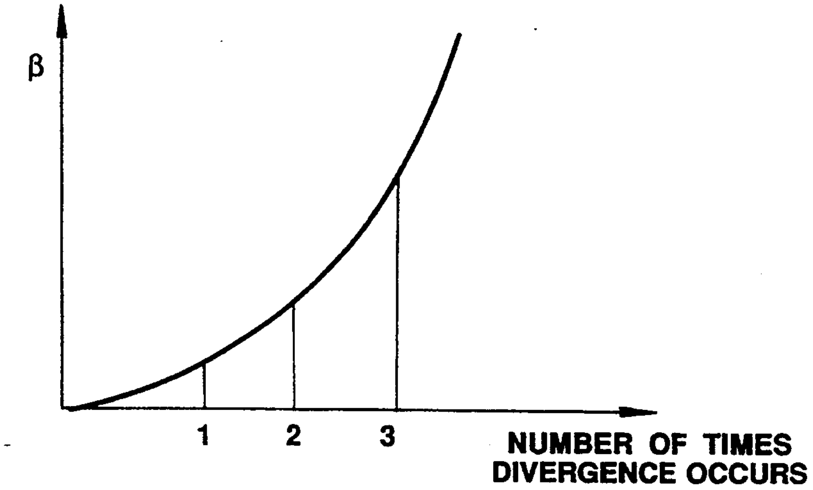
FIG. 9 is a characteristic graph of the effort coefficient varying with respect to an abruptly changing number of occurrences of divergences.
Figure 11:
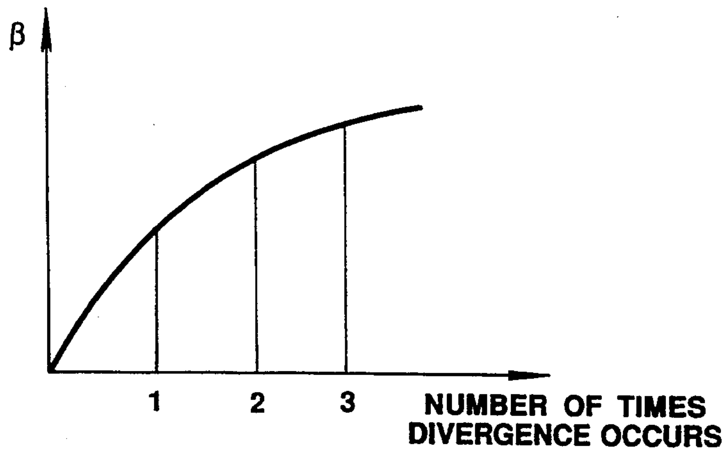
FIG. 11 is a characteristic graph of the effort coefficient varying with respect to an moderately changing number of occurrences of the divergences.

It is noted that FIG. 7, FIG. 9, and FIG. 11 show control patterns determined according to characteristics of enclosed space for which the noise control is carried out. FIG. 7 is concerned with the linear convergence space. FIG. 9 is concerned with the enclosed space in which an abrupt convergence easily appears. FIG. 11 is concerned with the enclosed space in which the divergence does not easily appear and in which an importance of the control effect has been placed.

It is also noted that in these drawings of FIG. 7 through FIG. 18, the symbol of $\beta$ is representatively used for all loud speakers but, in place of $\beta$, $\beta_m$ for each loud speaker may be used.

Figure 8:
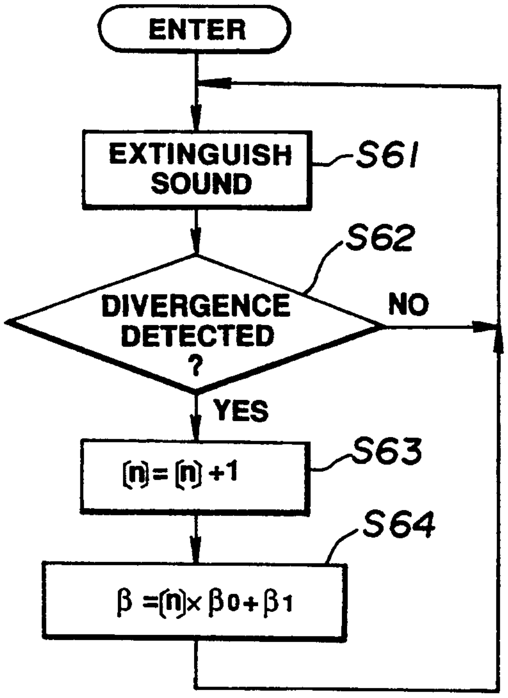
FIG. 8 is a flowchart of varying the effort coefficient executed by the control unit shown in FIG. 4.

The control pattern shown in FIG. 7 is executed in accordance with the flowchart of FIG. 8.

In a step S61, the extinguishing (noise canceling) operation is carried out by one step. In a step S62, the circuit 21 determines whether the divergence occurs even after the extinguishing (canceling out) operation is carried out by one step in the step S61. If not occur on divergence, the routine returns to the step S61. If divergence occurs, the routine goes to a step S62 in which the number of occurrences n is incremented by one. In a step S64, the effort coefficient $\beta$ is enlarged. Then, the step S61 is repeated. In this case, $\beta$ is derived by multiplying [n] with the reference effort coefficient $\beta_0$ and adding a predetermined quantity $\beta_1$ thereto. Hence, as shown in FIG. 7, the effort coefficient $\beta$ is linearly increased according to the number of occurrences [n] the divergences occur so that divergences in the vehicular compartment in which the divergences tend to linearly occur can effectively be suppressed.

Figure 10:
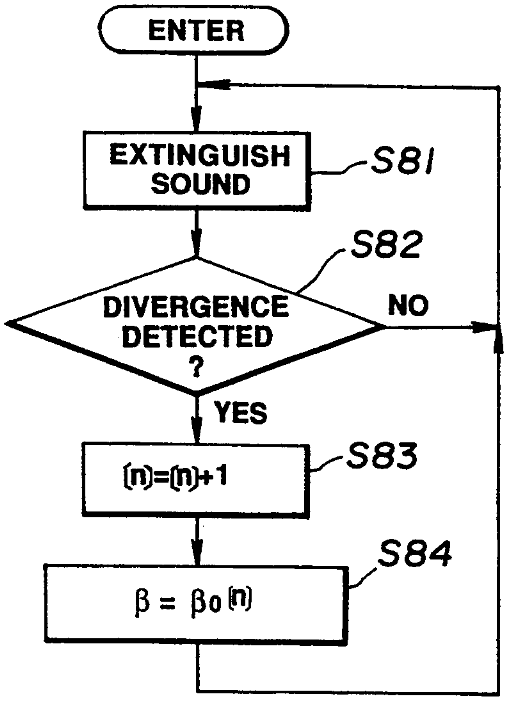
FIG. 10 is another flowchart of varying the effort coefficient executed by the control unit shown in FIG. 4.

The control pattern shown in FIG. 9 is executed according to the flowchart shown in FIG. 10.

In a step S81, the circuit 21 carries out the extinguishing (canceling out) operation described above.

In a step S82, the circuit 21 determines whether the divergence occurs even after the extinguishing operation is carried out. If not divergence occur, the routine returns to the step S81. If divergence occurs, the number of times [n] the occurrences of divergences [n] is incremented by one. In a step S84, $\beta$ is increased. Then, the step S81 is repeated. In this case, the reference effort coefficient $\beta$ is multiplied by the reference effort coefficient itself by the number of times [n] as: $\beta=\beta_0{}^{[n]}$. That is to say, even in the case of the abruptly occurred divergences , the effort coefficient $\beta$ is enlarged so as to suppress the divergence and the speedily and appropriate reduction control can be achieved.

Figure 12:
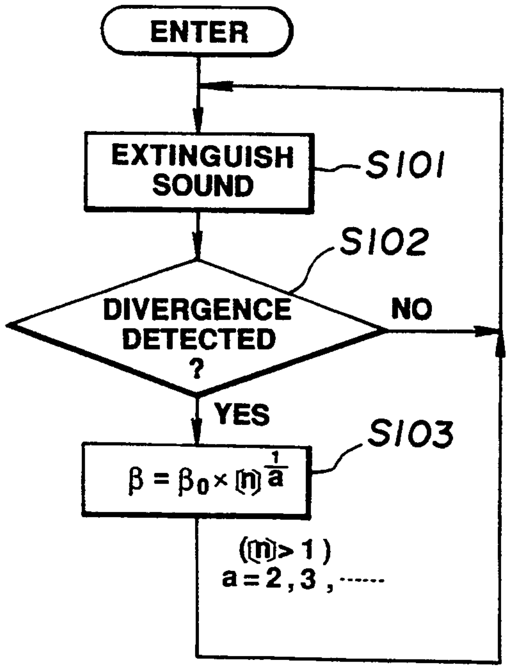
FIG. 12 is a still another flowchart of varying the effort coefficient executed by the control unit shown in FIG. 4.

The control pattern shown in FIG. 11 is executed by the flowchart shown in FIG. 12.

In a step S101, the circuit 21 carries out the extinguishing (noise canceling) operation.

Next, in a step S102, the circuit 21 determines whether the divergence occurs. If divergence does not occur, the routine returns to the step S101. If the divergence occurs, the routine goes to a step S103 in which the effort coefficient $\beta$ is enlarged. In this case, the effort coefficient $\beta$ is set as follows: $\beta=\beta_0\times[n]^{1/a}$ (provided that a is 2, or 3, - - - ).

Figure 13:
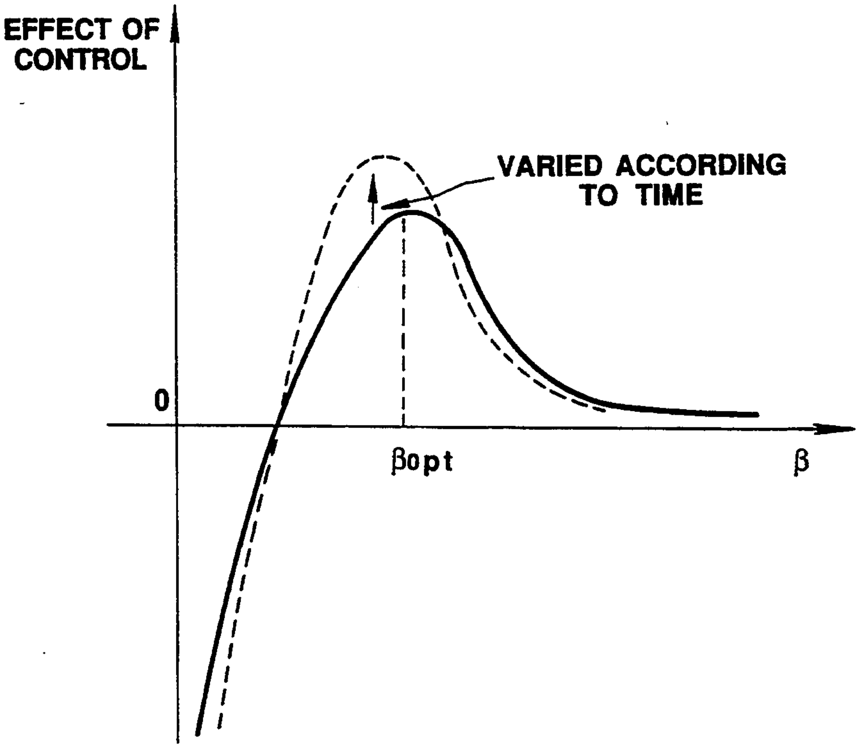
FIG. 13 is a characteristic graph of a relationship between the effort coefficient and effect of control.

Thereafter, the step S101 is again repeated. That is to say, as shown in FIG. 13, if the effort coefficient $\beta$ is enlarged, a peak (optimum value) of the control effect can be reached at a certain value of the effort coefficient $\beta_{Opt}$ and, even if $\beta$ becomes enlarged, the effect of control still exists. Hence, by this approach, the appropriate effort coefficient $\beta$ can be provided in any control state including the occurrence of divergence and the effect of control can be maximized along with suppressing the divergence.

Figure 14:
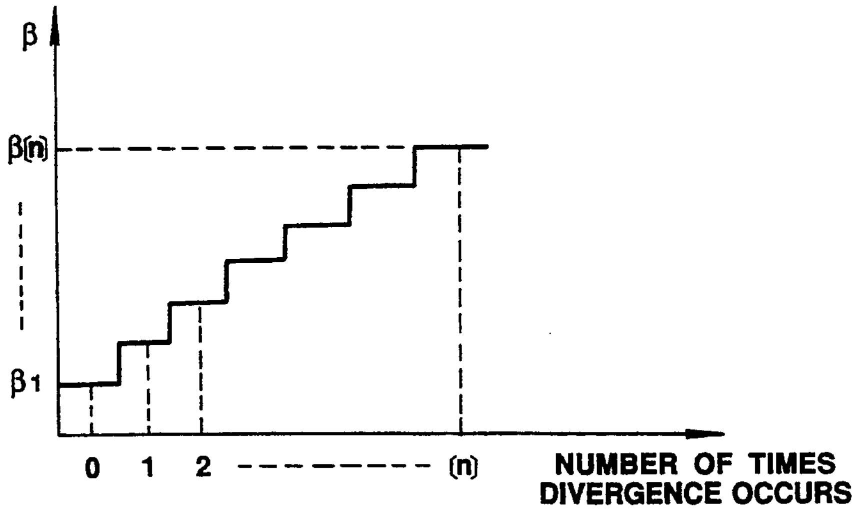
FIG. 14 is a characteristic graph of another example of a stepwise change in effort coefficient when the divergences linearly occur.

FIG. 14 shows a table map in a case when a map control operation is carried out. The table map shown in FIG. 14 is used when the circuit 21 executes the flowchart of FIG. 15.

Figure 15:
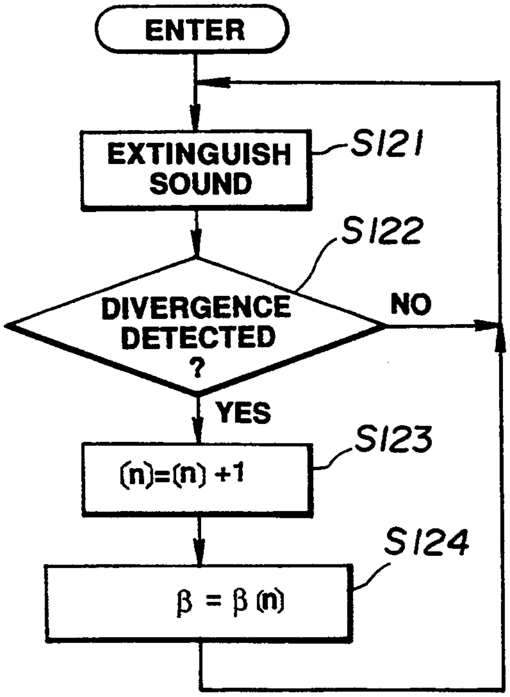
FIG. 15 is a further another flowchart of varying the effort coefficient.

In FIG. 15, steps S121 and S122 are the same as those in the steps S101 and S102. In a step S123, the circuit 21 increments the number of occurrences [n] by one.

In a step S124, the effort coefficient $\beta$ is stepwise enlarged as $\beta=\beta_{[n]}$ in accordance with the table map shown in FIG. 14. Hence, the same effect as in the case of FIG. 7 can be achieved and easy calculation can be achieved.

As described above, since the effort coefficient $\beta$ by which the speaker drive signals are multiplied is varied so that the contributivity (or contributibility, i.e., the manner to which the term representative of the speaker drive signals contribute to the performance function) of the speaker drive signals to the performance function Jm is changed according to the number of times the divergence occurs, a vector based on the convergence coefficient $\alpha$ and effort coefficient $\beta$ are converged to an optimum value and, thereby, the divergence can be suppressed.

Figure 16:
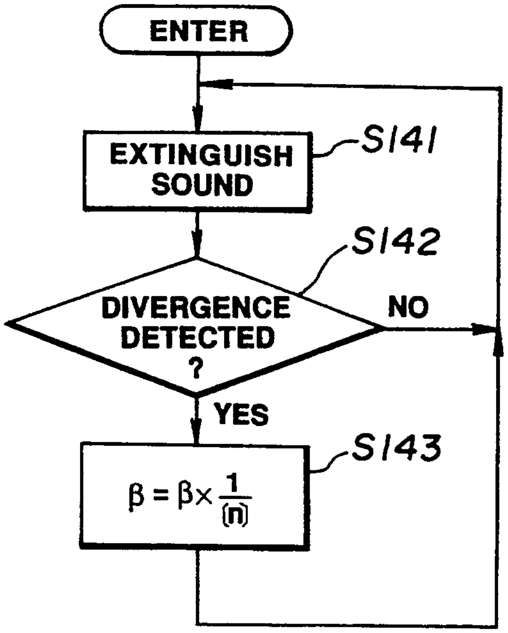
FIG. 16 is a further another flowchart executed by the control unit shown in FIG. 4 when the effort coefficient to multiply speaker drive signal in the performance function is reduced.

It is noted that in a case where the effort coefficient $\beta$ in the performance function is located at a denominator, i.e., the effort coefficient to multiply the speaker drive signals is expressed as $1/\beta$, the routine shown in FIG. 16 is executed.

In FIG. 16, steps S141 and S142 are the same as those steps S121 and S122. In a step S143, the effort coefficient is multiplied by 1/[n] ([n] is the number of times the divergences occur) so that the value of $\beta$ becomes smaller. In this case, since the small effort coefficient $\beta$ means the larger coefficient to multiply the speaker drive signals in the performance function and the same effect as in the case of FIGS. 14 and 15 can be achieved.

Figure 17:
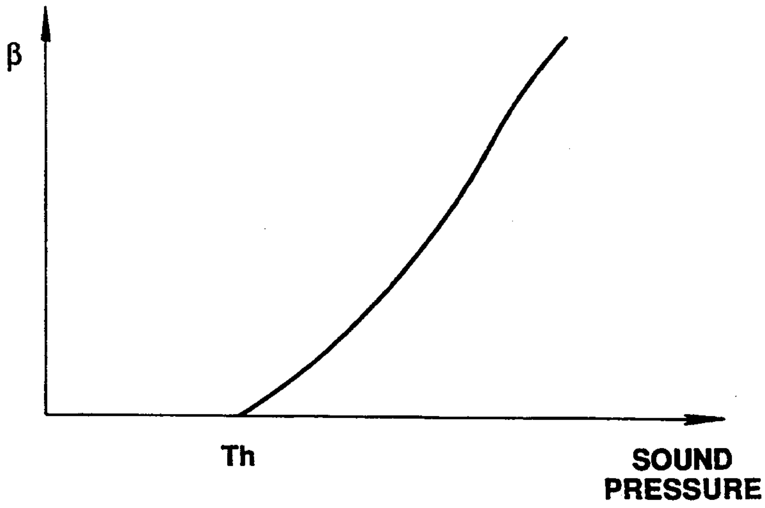
FIG. 17 is a characteristic graph of a relationship between a change in sound pressure and effort coefficient in a case when the divergence is perceived according to a sound pressure.

It is noted that although, in the preferred embodiment, the effort coefficient $\beta$ is varied according to the number of times the divergences occur, the sound pressure at the evaluating point is detected and the effort coefficient $\beta$ may be varied when thereafter the sound pressure level exceeds a predetermined value Th as appreciated from FIG. 17.

Figure 18:
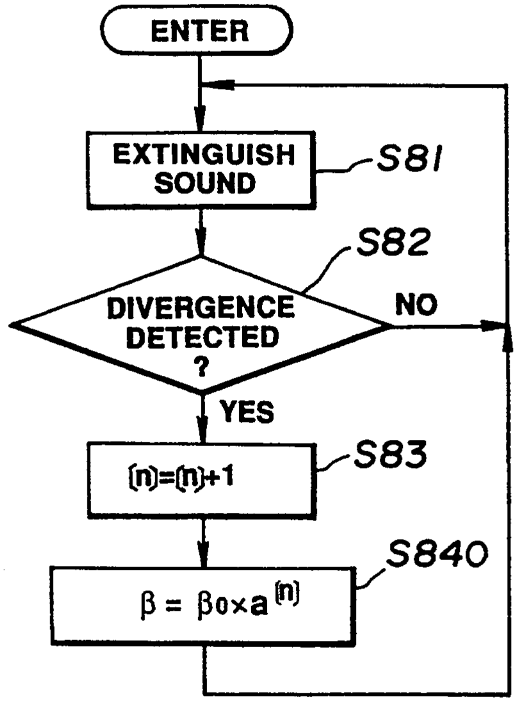
FIG. 18 is a modification of the flowchart of varying the effort coefficient for FIG. 10.

FIG. 18 shows a modification of the flowchart of FIG. 10.

In FIG. 18, the steps S81 through S83 are the same as those in FIG. 10. However, in a step S840, the effort coefficient $\beta$ is set as follows:

$$\beta=\beta_0\times a^{[n]}.$$

The present invention is not limited to the preferred embodiment.

For example, although, in the preferred embodiment, two digital filters are used and Multiple Error Filtered-X LMS algorithm has been described, the control apparatus using the single filter may also be established.

In addition, even in a case where the evaluating point at which the noise reduction control is achieved is spatially separated from any one of the microphones, the residual noise at the evaluating point may be estimated on the basis of the predetermined value and the noise reduction control may be carried out.

Although, in the preferred embodiment, the divergence detecting circuit 21 is used as the divergence detecting means, for example, another circuit for predicting or detecting the occurrence of divergence according to a change in the number of occupants in the vehicle compartment and/or a change in temperature in the vehicle compartment and modifying the contributivity of speaker drive signals to the performance function may be alternatively used.

It is natural that although, in the preferred embodiment, the level on the basis of which the circuit 21 determines whether the divergence occurs is constant, the level (also expressed as the predetermined value of $E_0$) be varied according to environmental condition of the vehicle compartment.

In addition, in the equation (9), k may denote the effort coefficient in place of $\beta$, wherein $k=2\beta\ \alpha$ or $K=\beta\alpha$, and k may be varied so that the divergence may be suppressed.

Another LMS algorithm may alternatively be used in place of the Multiple Error Filtered-X LMS algorithm used in the preferred embodiment.

Furthermore, although, in the preferred embodiment, the loud speakers *7a* through *7d* are installed on respective door inner portions of the vehicular compartment and the microphones *8a* through *8h* are disposed on the head rest positions of the respective occupant seats $S_1$ through $S_4$, the loud speakers may be disposed on other appropriate positions (e.g., front portions of the front occupant seats $S_1$, $S_2$ which are generally adjacent to an engine room) in the enclosed space than the door inner portions and the microphones may also be disposed on other appropriate positions (e.g., ceiling portions generally adjancent to the occupants' ears when the occupants get on the vehicle).

As described hereinabove, the actively noise reducing apparatus according to the present invention has the following effect that the contributivity changing means can change the contributivity of the control sound source drive signals to the performance function. For example, when the transfer function in the enclosed space is changed, the contributivity can accordingly be changed and the more appropriate noise control can be achieved.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

TABLE 1

$$e_l(n) = e_{pl}(n) + \sum_{m=1}^{M}\sum_{j=0}^{Jc-1} C_{lmj}\cdot\left\{\sum_{i=o}^{Ik-1} W_{mi}\cdot x_p(n-j-i)\right\} \quad (1)$$

$$J_e = E\left[\sum_{l=1}^{L}\{e_l(n)\}^2\right] \quad (2)$$

$$\frac{\partial J_e}{\partial W_{mi}} = \sum_{l=1}^{L} 2e_l(n)\frac{\partial e_l(n)}{\partial W_{mi}} \quad (3)$$

$$\frac{\partial e_l(n)}{\partial W_{mi}} = \sum_{j=0}^{Jc-1} C_{lmj}\cdot X_p(n-j-i) \quad (4)$$

$$W_{mi}(n+1) = W_{mi}(n) - \alpha\cdot\sum_{l=1}^{L}\gamma_l e_l(n)\cdot r_{lm}(n-i) \quad (5)$$

$$\sum_{l=1}^{L} e_l(n)\cdot r_{lm}(n-i) \quad (6)$$

$$J_m = E\left\{\sum_{l=1}^{L}(e_l(n))^2 + \beta\cdot(y_m(n))^2\right\} \quad (7)$$

TABLE 2

$$e_l(n) = d(n) + \sum_{m=1}^{M}\sum_{j=0}^{J-1} C_{lmj}\cdot y_m(n-j) \quad (8)$$

$$J_m = E\left\{\sum_{l=1}^{L}(e_l(n))^2 + \beta_m\cdot(y_m(n))^2\right\} \quad (9)$$

$$y_m(n) = \sum_{i=0}^{I-1} W_{mi}\cdot x(n-i) \quad (10)$$

$$J_m = E\left(\sum_{l=1}^{L}\left[d(n) + \sum_{j=0}^{J-1} C_{lmj}\cdot\left\{\sum_{i=0}^{I-1} W_{mi}\cdot x(n-i-j)\right\}\right]^2 + \beta_m\cdot\left\{\sum_{i=0}^{I-1} W_{mi}\cdot x(n-i)\right\}^2\right) \quad (11)$$

$$W_{mi}(n+1) = W_{mi}(n) - \alpha\frac{\partial J_m(n)}{\partial W_{mi}(n)} \quad (12)$$

TABLE 2-continued $$\frac{\partial J_m}{\partial W_{mi}} = \frac{\partial}{\partial W_{mi}}\left\{\sum_{l=1}^{L}(e_l(n))^2 + \beta_m\cdot(y_m(n))^2\right\} = \sum_{l=1}^{L} el(n)\cdot 2\frac{\partial}{\partial W_{mi}}\{e_l(n)\} + \beta_m\cdot y_m(n)\cdot 2\frac{\partial}{\partial W_{mi}}\{y_m(n)\} \quad (13)$$

TABLE 3

$$\frac{\partial}{\partial W_{mi}}\{e_l(n)\} = \frac{\partial}{\partial W_{mi}}\left[d(n) + \sum_{j=0}^{J-1} C_{lmj}\cdot\left\{\sum_{i=0}^{I-1} W_{mi}\cdot x(n-i-j)\right\}\right] = \sum_{j=0}^{J-1} C_{lmj}\cdot x(n-i-j) \quad (14)$$

$$\frac{\partial}{\partial W_{mi}}\left\{\sum_{i=0}^{I-1} W_{mi}\cdot x(n-i)\right\} = x(n-i) \quad (15)$$

$$R_{lm}(n) = \sum_{j=0}^{J-1} C_{lmj}\cdot x(n-j) \quad (16)$$

$$\sum_{j=0}^{J-1} C_{lmj}\cdot x(n-i-j) = R_{lm}(n-i) \quad (17)$$

$$\frac{\partial J_m}{\partial W_{mi}} = 2\sum_{l=1}^{L} e_l(n)\cdot R_{lm}(n-i) + 2\beta_m\cdot y_m(n)\cdot x(n-i) \quad (18)$$

$$W_{mi}(n+1) = W_{mi}(n) - \alpha\left\{2\sum_{l=1}^{L} e_l(n)\cdot R_{lm}(n-i) + 2\beta_m\cdot y_m(n)\cdot x(n-i)\right\} = W_{mi}(n) - 2\alpha\sum_{l=1}^{L} e_l(n)\cdot R_{lm}(n-i) - 2\beta_m\,\alpha\cdot y_m(n)\cdot x(n-i) \quad (19)$$

What is claimed is:

1. An apparatus for actively reducing noise for an interior of enclosed space, comprising:

a) control sound source means for generating a control sound, to interfere with the noise according to a drive signal input thereto, so as to reduce the noise propagated into the interior of enclosed space at an evaluating area in the interior of enclosed space at which a degree of a residual noise sound is evaluated;

b) residual noise detecting means for detecting the residual noise sound at a predetermined area of the interior of the enclosed space after the noise interference is carried out by the control sound source means and outputting the detected residual noise sound as a residual noise signal;

c) reference signal detecting means for detecting a signal related to a noise source and processing the detected signal as a reference signal;

d) controlling means for outputting the drive signal to said control sound source means on the basis of the output residual noise signal of said residual noise detecting means, the reference signal of said reference signal detecting means, and the drive signal output from the controlling means itself to the control sound source so that a performance function is minimized, said performance function being established thereby on the basis of the output residual noise signal of said residual noise detecting means and the drive signal output to said control sound source means;

e) changing means for directly changing a contributivity of the drive signal to the performance function, and further including divergence detecting means for predictively monitoring whether a divergence of control sound derived from said control sound source means occurs at the evaluating area and wherein said changing means changes the contributivity of the drive signal to the performance function according to a result of the monitoring by said divergence detecting means.

2. An apparatus for actively reducing noise for an interior of enclosed space as set forth in claim 1, wherein said changing means includes a variable effort coefficient by which a term of the control sound source means drive signal in the performance function is multiplied.

3. An apparatus for actively reducing noise for an interior of enclosed space as set forth in claim 1, which further includes a manually operable switch and wherein said changing means changes the contributivity of the drive signal output to said control sound source means to the performance function in response to an ON state of the manually operable switch.

4. An apparatus for actively reducing noise sound for a vehicular compartment as set forth in claim 1, wherein said controlling means includes an FIR digital adaptive filter having variable filter coefficients and outputting the drive signals $y_m(n-J)$ to said M numbers of loud speakers as follows:

$$y_m(n) = \sum_{i=0}^{I-1} W_{mi} \cdot x(n-i),$$

wherein $y_m(n)$ denotes the drive signal output to the m number loud speaker at a sampling time of n, $W_{mi}$ denotes an i number filter coefficient of the FIR digital adaptive filter, I denotes a number of taps of the FIR adaptive filter ( i=0, 1,- - -, I-1).

5. An apparatus for actively reducing noise sound for a vehicular compartment as set forth in claim 4, wherein said control means establishes the performance function Jm as follows:

$$Jm = E\left[\left\{ \sum_{l=1}^{L} (e_l(n))^2 + \beta_m \cdot (y_m(n))^2 \right\}\right],$$

wherein E denotes an expectation value and $\beta_m$ denotes an effort coefficient.

6. An apparatus for actively reducing noise sound for a vehicular compartment as set forth in claim 5, wherein said filter coefficient $W_{mi}(n)$ of the FIR digital adaptive filter is updated using a steepest descent method as follows:

$$W_{mi}(n+1) = W_{mi}(n) - \alpha \partial J_m(n) / \partial W_{mi}(n) =$$
$$W_{mi}(n) - 2\alpha \sum_{l=1}^{L} e_l(n) \cdot R_{lm}(n-i) - 2\beta\alpha \cdot y_m(n) \cdot x(n-i),$$

wherein $\alpha$ denotes a convergence coefficient $\beta$ is an effort coefficient and $R_{lm}$ (n−i) is expressed as follows:

$$R_{lm}(n-i) = \sum_{j=0}^{J-1} c_{lmj} \cdot x(n-i-j).$$

7. An apparatus for actively reducing noise sound for a vehicular compartment as set forth in claim 6, wherein said effort coefficient $\beta$ is expressed as k and wherein k is one of $2\alpha$ and $\alpha$.

8. An apparatus for actively reducing noise sound for a vehicular compartment as set forth in claim 7, wherein $\alpha$ is expressed as one of the expressions $\alpha_{mi}$ so that the convergence coefficient $\alpha$ varies according to loud speaker number m and $\alpha$l so that the convergence coefficient $\alpha$ varies according to microphone number l.

9. An apparatus for actively reducing noise for an interior of enclosed space, comprising:

a) control sound source means for generating a control sound, to interfere with the noise according to a drive signal input thereto, so as to reduce the noise propagated into the interior of enclosed space at an evaluating area in the interior of enclosed space at which a degree of a residual noise sound is evaluated;

b) residual noise detecting means for detecting the residual noise sound at a predetermined area of the interior of the enclosed space after the noise interference is carried out by the control sound source means and outputting the detected residual noise sound as a residual noise signal;

c) reference signal detecting means for detecting a signal related to a noise source and processing the detected signal as a reference signal;

d) controlling means for outputting the drive signal to said control sound source means on the basis of the output residual noise signal of said residual noise detecting means and the reference signal of said reference signal detecting means so that a performance function is minimized, said performance function being established thereby on the basis of the output residual noise signal of said residual noise detecting means and the drive signal output to said control sound source means and including a term of the drive signal output to said control sound source means multiplied by an effort coefficient; and e) changing means for directly changing the effort coefficient so that a contributivity of the drive signal means to the performance function is varied, and further including divergence detecting means for predictively monitoring whether a divergence of control sound derived from said control sound source means occurs at the evaluating area and wherein said changing means changes the contributivity of the drive signal to the performance function according to a result of the monitoring by said divergence detecting means.

10. An apparatus for actively reducing noise for an interior of enclosed space as set forth in claim 9, wherein said changing means enlarges the contributivity of the drive signal output to said control sound source means to the performance function on the basis of the output divergence signal of said divergence detecting means.

11. An apparatus for actively reducing noise for an interior of enclosed space as set forth in claim 10, wherein said changing means enlarges the effort coefficient on the basis of the output divergence signal of said divergence detecting means.

12. An apparatus for actively reducing noise for an interior of enclosed space as set forth in claim 11, wherein said changing means enlarges the contributivity of the drive signal output to said control sound source means to the performance function according to a number of times the divergence signals of the divergence detecting means are output.

13. An apparatus for actively reducing noise for an interior of enclosed space as set forth in claim 12, wherein said changing means enlarges the effort coefficient according to the number of times the divergence signals of the divergence detecting means are output.

14. An apparatus for actively reducing noise sound for a vehicular compartment, comprising:

a) an electrical-acoustic transducer which generates a control sound, to interfere with the noise sound in response to a drive signal input thereto, to be interfered with the noise sound in response to a drive signal so as to reduce the noise sound at respective evaluating points of location in the vehicular compartment;

b) an acoustic-electrical transducer which detects a residual noise at predetermined positions of the vehicular compartment after the interference of the control sound with the noise sound by said electrical-acoustic transducer and output a residual noise signal indicating the detected residual noise;

c) detecting means for detecting a signal related to a noise generating state from a vehicular noise source and outputting a discrete reference signal indicating the signal related to the noise generating state;

d) controlling means for establishing an performance function on the basis of the residual noise signal and transducer drive signal and for outputting the drive signal to said electrical-acoustic transducer so that the performance function is minimized on the basis of the residual noise signal of said acoustic-electrical transducer, the reference signal of said detecting means, and, furthermore, the electrical-acoustic transducer drive signal;

e) divergence detecting means for detecting an occurrence of divergence of the control sounds at evaluating points of location and outputting a divergence indicative signal whenever the divergence occurs; and f) contributivity changing means for changing a contributivity of the electrical-acoustic transducer drive signal to the performance function in response to the divergence indicative signal derived from said divergence detecting means.

15. An apparatus for actively reducing noise sound for a vehicular compartment as set forth in claim 14, wherein said electrical-acoustic transducer comprises M numbers of loud speakers installed on respective door portions of the vehicular compartment so as to face toward vehicular occupant seats and said acoustic-electrical transducer comprises L numbers of microphones installed at respective head rest portions of the vehicular occupant seats as evaluating points of locations, and said signal detecting means comprises a crank angle sensor for outputting the reference signal x whenever an engine crankshaft has rotated through a predetermined angle.

16. An apparatus for actively reducing noise sound for a vehicular compartment as set forth in claim 14, wherein said electrical-acoustic transducer comprises M numbers of loud speakers installed on respective predetermined positions of the vehicular compartment which are adjacent to the vehicular noise source and said acoustic-electrical transducer comprises L numbers of microphones installed at respective evaluating points of locations which are adjacent to ears portions of occupants when the occupants take corresponding seats of the vehicular compartment, and said signal detecting means comprises a crank angle sensor for outputting the reference signal x whenever an engine crankshaft has rotated through a predetermined angle.

17. An apparatus for actively reducing noise sound for a vehicular compartment as set forth in claim 16, wherein the residual noise signal $e_l(n)$ detected by an l-th microphone is expressed as follows:

$$e_l(n) = d(n) + \sum_{j=0}^{J-1} (c_{lmj}) \cdot y_m(n-j),$$

wherein d(n) denotes the residual noise signal detected by the l-th microphone when the control sound derived from any one of the M loud speakers is not present, $y_m(n-j)$ denotes the drive signal output to the m-th loudspeaker at a sampling time of (n−j), and $c_{lmj}$ denotes a filter coefficient corresponding to a j-th (i=0, 1, - - -, J−1) transfer function $H_{lm}$ between the m-th loud speaker and the l-th microphone.

18. An apparatus for actively reducing a noise for a vehicular compartment as set forth in claim 15, wherein said divergence detecting means calculates the following:

$$\sum_{l=1}^{L} (e_l(n))^2,$$

determines whether $$\sum_{l=1}^{L} (e_l(n))^2 \geqq E_0,$$

wherein $E_0$ denotes a predetermined value, determines whether a number of times [M] the occurrence of $$\sum_{l=1}^{L} (e_l(n))^2 \geqq E_0$$

exceeds a predetermined number of times [$M_0$], and outputs the divergence indicative signal when the number of times [M] the occurrence of $$\sum_{l=1}^{L} (e_l(n))^2 \geqq E_0$$

exceeds the predetermined number of times [$M_0$].

19. An apparatus for actively reducing noise sound for a vehicular compartment as set forth in claim 18, wherein said effort coefficient $\beta_m$ is varied when the divergence indicative signal is output from the divergence detecting means.

20. An apparatus for actively reducing noise sound for a vehicular compartment as set forth in claim 19, wherein said effort coefficient $\beta_m$ is varied in the following way:

$\beta_m = \beta_{m0}^{[n]}$, wherein $\beta_{m0}$ denotes a reference effort coefficient and [n] denotes the number of times the divergence indicative signal is output.

21. An apparatus for actively reducing noise sound for a vehicular compartment as set forth in claim 19, wherein said effort coefficient $\beta_m$ is varied in the following way:

$$\beta_m = \beta_{m0} x [n]^{1/a},$$

[n] denotes the number of times the divergence indicative signal is output and a is an integer exceeding one.

22. An apparatus for actively reducing noise sound for a vehicle compartment as set forth in claim 19, wherein said effort coefficient $\beta_m$ is varied stepwise according to a number of times the divergence indicative signal is output in the following way:

$$\beta_m = \beta_{m\{n\}},$$

wherein {n} denotes the number of times the divergence indicative signal is output.

23. An apparatus for actively reducing noise-sound for a vehicular compartment as set forth in claim 19, wherein said effort coefficient $\beta_m$ is varied in the following way so as to be stepwise increased as the number of times n the divergence indicative signal is output is increased:

$$\beta_m = \beta_{m[n]},$$

wherein [n] denotes the number of times the divergence indicative signal is output.

24. An apparatus for actively reducing noise sound for a vehicular compartment as set forth in claim 19, wherein said effort coefficient $\beta_m$ is varied in the following way:

$$\beta_m = \beta_m x\ 1/[n],$$

wherein [n] denotes the number of times the divergence indicative signal is output.

25. An apparatus for actively reducing noise sound for a vehicular compartment as set forth in claim 19, wherein said divergence detecting means detects a sound pressure level at at least one evaluating point of location and outputs the divergence indicative signal when the sound pressure thereat exceeds a predetermined level and said effort coefficient $\beta_m$ is varied when the divergence indicative signal is output.

26. An apparatus for actively reducing noise sound for a vehicular compartment as set forth in claim 19, wherein said effort coefficient $\beta_m$ is varied in the following way:

$$\beta_m = [n] x\ \beta_{m0} + \beta_{ml},$$

wherein [n] denotes the number of times the divergence indicative signal is output, $\beta_{m0}$ denotes a reference effort coefficient, and $\beta_{ml}$ denotes a predetermined fixed value of the effort coefficient.

27. An apparatus for actively reducing noise for an interior of enclosed space, comprising:

a) control sound source means for generating a control sound to interfere with the noise according to a source drive signal input thereto for reducing the noise propagated into the interior of enclosed space at an evaluating area in the interior of enclosed space at which a degree of a residual noise sound is evaluated;

b) residual noise detecting means for detecting the residual noise sound at a predetermined area of the interior of the enclosed space after noise interference is carried out by the control sound source means, said residual noise detecting means outputting the detected residual noise sound as a residual noise signal;

c) reference signal detecting means for detecting a signal related to a noise source and processing the detected signal as a reference signal;

d) controlling means for outputting said source drive signal to said control sound source means, said controlling means operating for minimizing a performance function by generating said source drive signal in response to said residual noise signal outputted by said residual noise detecting means, said reference signal outputted by said reference signal detecting means, and said source drive signal outputted by said controlling means itself, said performance function being established thereby on the basis of said residual noise signal outputted by said residual noise detecting means and said source drive signal outputted to said control sound source means;

e) changing means for changing a contributivity of said source drive signal to said performance function, and f) divergence detecting means for predictively monitoring whether a divergence of control sound, derived from said control sound source means, occurs at the evaluating area from a state in which the performance function becomes minimized, g) wherein said changing means is responsive to a monitoring result of said divergence detecting means for changing the contributivity of said drive signal to said performance function.

* * * * *